US012515072B2

(12) United States Patent
Marash et al.

(10) Patent No.: US 12,515,072 B2
(45) Date of Patent: Jan. 6, 2026

(54) TELETHERAPY PATIENT SUPPORT AND METHOD

(71) Applicant: P-CURE LTD., Shilat (IL)

(72) Inventors: Michael Marash, Rishon Le'tzion (IL); Yael Braude, Rosh Ha'ayin (IL)

(73) Assignee: P-CURE LTD., Shilat (IL)

( * ) Notice: Subject to any disclaimer, the term of this patent is extended or adjusted under 35 U.S.C. 154(b) by 369 days.

(21) Appl. No.: 18/023,473

(22) PCT Filed: Aug. 26, 2021

(86) PCT No.: PCT/IL2021/051051

§ 371 (c)(1),
(2) Date: Feb. 27, 2023

(87) PCT Pub. No.: WO2022/044016

PCT Pub. Date: Mar. 3, 2022

(65) Prior Publication Data

US 2023/0310884 A1 Oct. 5, 2023

Related U.S. Application Data

(60) Provisional application No. 63/070,853, filed on Aug. 27, 2020.

(51) Int. Cl.

*A61N 5/10* (2006.01)
*G16H 20/40* (2018.01)
*G16H 40/63* (2018.01)

(52) U.S. Cl.

CPC ............... *A61N 5/10* (2013.01); *G16H 20/40* (2018.01); *G16H 40/63* (2018.01); *A61N 2005/1074* (2013.01); *A61N 2005/1097* (2013.01)

(58) Field of Classification Search

CPC .......... G16H 20/40; G16H 40/63; A61F 5/37; A61N 2005/1074; A61N 2005/1097;
(Continued)

(56) References Cited

U.S. PATENT DOCUMENTS 3,948,559 A 4/1976 Hain et al.
6,295,671 B1 10/2001 Reesby et al.
(Continued)

FOREIGN PATENT DOCUMENTS

WO 9953998 A1 10/1999
WO WO-2019123464 A1 * 6/2019 ........... A61B 6/0487

OTHER PUBLICATIONS

International Search Report of PCT/IL2021/051051 Completed Dec. 28, 2021; Mailed Dec. 28, 2021 4 Pages.
(Continued)

*Primary Examiner* — Ophelia A Hawthorne
(74) *Attorney, Agent, or Firm* — The Roy Gross Law Firm, LLC; Roy D. Gross

(57) ABSTRACT

A teletherapy patient support constituted of: a pelvis support member exhibiting a first face and a second face opposing the first face; a torso support member extending from the pelvis support member and facing the first face of the pelvis support member; a first leg support extending from the pelvis support member and facing the second face of the pelvis support member; and a second leg support exhibiting at least one connection member, wherein the second leg support further exhibits at least one receptacle, the pelvis support member arranged to be alternately: attached to the pelvis support member by the at least one connection member being positioned within the at least one receptacle of the pelvis support member; and detached from the pelvis
(Continued)

support member by the at least one connection member not being positioned within the at least one receptacle of the pelvis support member.

16 Claims, 6 Drawing Sheets

(58) Field of Classification Search
CPC ...... A61N 5/1049; A61N 5/107; A61B 6/032; A61B 6/0428; A61B 6/0478; A61B 6/505; A61G 7/015; A61G 7/018; A61G 13/123; A61G 15/02
See application file for complete search history.

(56) References Cited

U.S. PATENT DOCUMENTS

| | | | |
|---|---|---|---|
| 2003/0164459 | A1 | 9/2003 | Schardt et al. |
| 2015/0238380 | A1 | 8/2015 | Kreuzer et al. |
| 2019/0231217 | A1 | 8/2019 | Sadlik et al. |

OTHER PUBLICATIONS

Written Opinion of PCT/IL2021/051051 Completed Dec. 28, 2021; Mailed Dec. 28, 2021 5 Pages.
European Search Report for International Application No. PCT/IL2021/051051—completion Jul. 23, 2024.

* cited by examiner

UPRIGHT RANGE

RECLINED RANGE

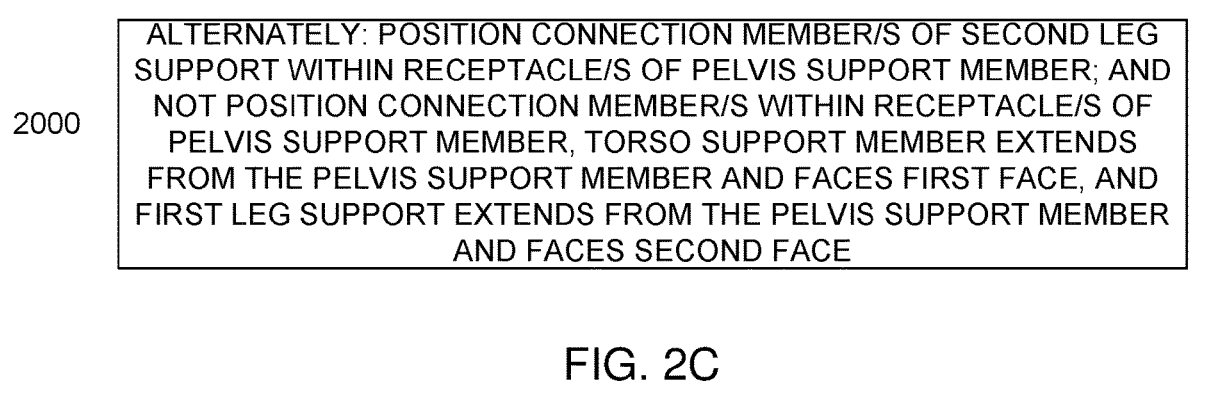

2000

ALTERNATELY: POSITION CONNECTION MEMBER/S OF SECOND LEG SUPPORT WITHIN RECEPTACLE/S OF PELVIS SUPPORT MEMBER; AND NOT POSITION CONNECTION MEMBER/S WITHIN RECEPTACLE/S OF PELVIS SUPPORT MEMBER, TORSO SUPPORT MEMBER EXTENDS FROM THE PELVIS SUPPORT MEMBER AND FACES FIRST FACE, AND FIRST LEG SUPPORT EXTENDS FROM THE PELVIS SUPPORT MEMBER AND FACES SECOND FACE

FIG. 2C

TELETHERAPY PATIENT SUPPORT AND METHOD

CROSS-REFERENCE TO RELATED APPLICATIONS

This application is a National Phase of PCT Patent Application No. PCT/IL2021/051051 having International filing date of Aug. 26, 2021, which claims the benefit of priority of U.S. Provisional Patent Application No. 63/070,853, filed Aug. 27, 2020, titled "TELETHERAPY PATIENT SUPPORT AND METHOD", the contents of which are incorporated herein by reference in their entirety.

TECHNICAL FIELD

The invention relates generally to the field of teletherapy and in particular to a teletherapy patient support and method.

BACKGROUND

Teletherapy is defined as a treatment methodology in which an irradiation source is at a distance from the body to be treated. X-rays and electron beams have long been used in teletherapy to treat various cancers, and more recently the use of heavy particles in teletherapy, such as protons, has increased.

The radiation can be focused to a target volume of variable penetration depth. In this way the dose profile can be matched closely to the target volume with a high precision. In order to ensure complete irradiation of the target growth, i.e. the target volume, a plurality of beams arriving at the target growth from several different directions is preferred. The point at which the plurality of beams intersects, whether they are beamed sequentially or simultaneously, is termed the isocenter, and to maximize biological effectiveness the isocenter is to be precisely collocated with the target growth.

Irradiation treatment is performed on a target growth in a well-defined process. In a first stage, known as the treatment planning stage, the target growth is imaged and a treatment plan is defined, comprising dosage, patient position, and irradiation angles. Furthermore, placement markers are defined, so as to ensure that subsequent irradiation sessions are properly targeted. Irradiation is then performed, responsive to the developed treatment plan, at a plurality of treatment sessions over a period of time, each treatment session being known as a fraction. At each such fraction, care must be taken to ensure proper patient positioning, responsive to the placement markers, so as to avoid damage to organs in vicinity of the target growth. Positioning of the patient responsive to the markers is performed based on visualization of the patient, responsive to the defined markers.

Particularly, during each fraction, the patient is positioned on a patient support member, such as a bed, in a setup position. The setup position is preferably identical to the patient position during the imaging of the treatment planning stage, except that the setup position is in the treatment room and the center of the target growth is positioned at the isocenter of the irradiation source. The setup position of the patient is typically verified by imaging and/or positioning devices. What is desired, and not provided by the prior art, is a patient support that allows teletherapy and imaging at various angles, and in various patient positions.

U.S. patent S/N U.S. Pat. No. 7,847,275, granted Dec. 7, 2010 to Lifshitz et al., the entire contents of which are incorporated herein by reference, is addressed to a teletherapy positioning apparatus which is adapted to translate a patient support member along any of three orthogonal axes and rotate the patient support member at least 180 degrees about each of three axes so as to position the patient support member with respect to a fixed treatment beam, thus allowing a patient who is lying down to be treated at any desired angle. Although this allows treatment at a variety of angles, it is limited to a flat patient support member where the patient is lying down.

SUMMARY OF THE INVENTION

Accordingly, it is a principal object of the present invention to overcome disadvantages of prior art methods and arrangements of teletherapy. This is provided in one embodiment by a teletherapy patient support, the teletherapy patient support comprising: a pelvis support member exhibiting a first face and a second face opposing the first face; a torso support member extending from the pelvis support member and facing the first face of the pelvis support member; a first leg support extending from the pelvis support member and facing the second face of the pelvis support member; and a second leg support exhibiting at least one connection member, wherein the second leg support further exhibits at least one receptacle, the pelvis support member arranged to be alternately: attached to the pelvis support member by the at least one connection member being positioned within the at least one receptacle of the pelvis support member; and detached from the pelvis support member by the at least one connection member not being positioned within the at least one receptacle of the pelvis support member.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 2C illustrates a high level flow chart of a second teletherapy patient support method, in accordance with certain embodiments.

DETAILED DESCRIPTION OF THE PREFERRED EMBODIMENTS

Figure 1A:
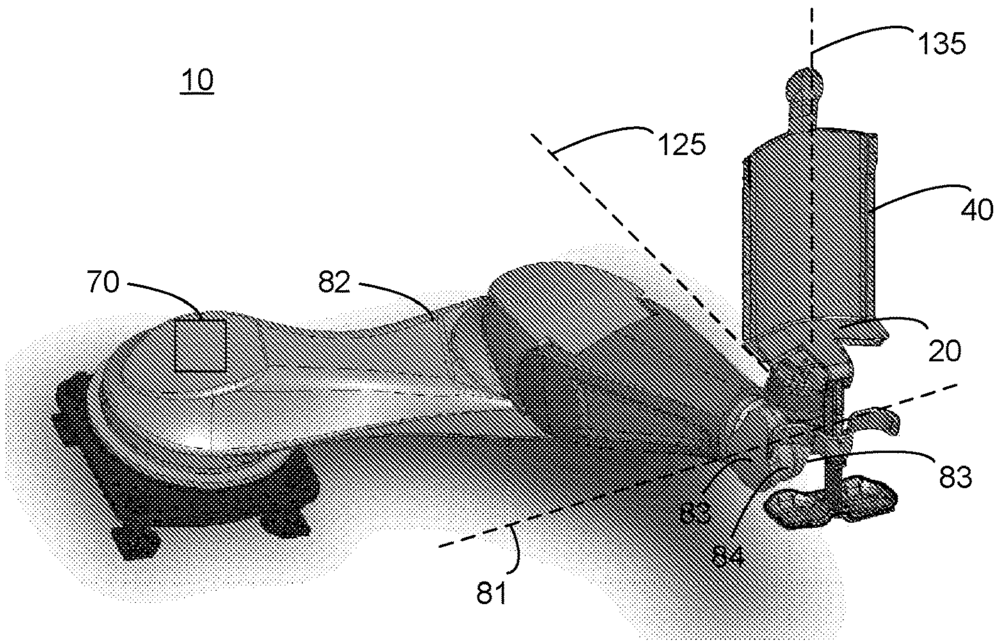
FIGS. 1A-1M illustrate various high level views of a teletherapy patient support, in accordance with certain embodiments.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1B:
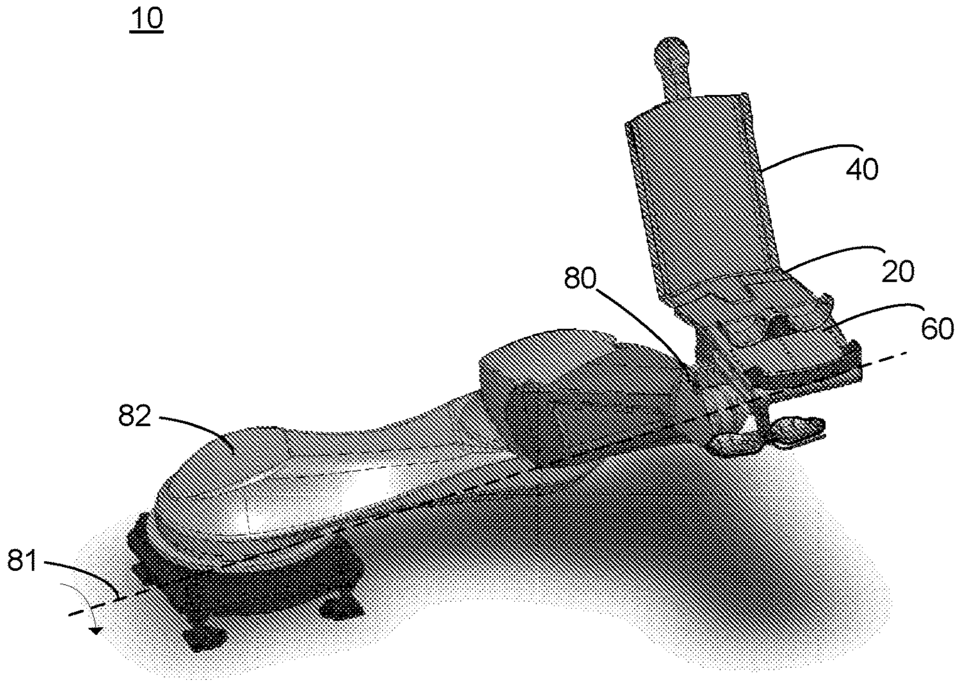
Figure 1C:
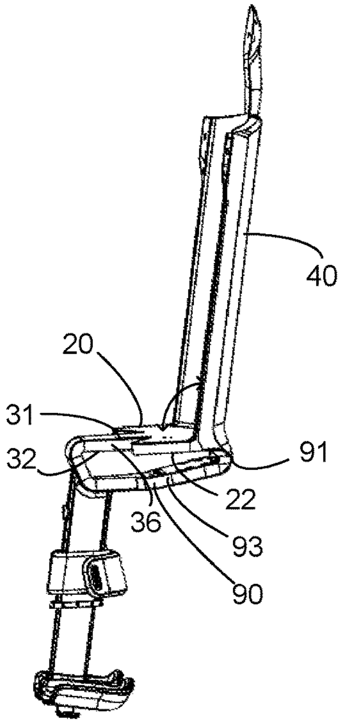
Figure 1D:
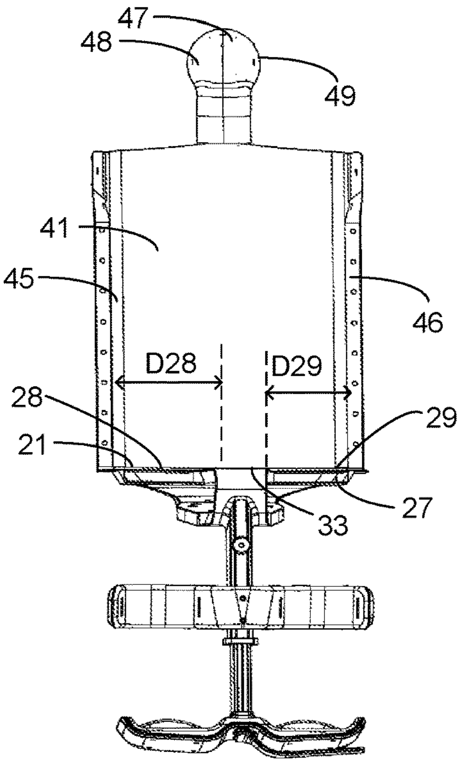
Figure 1E:
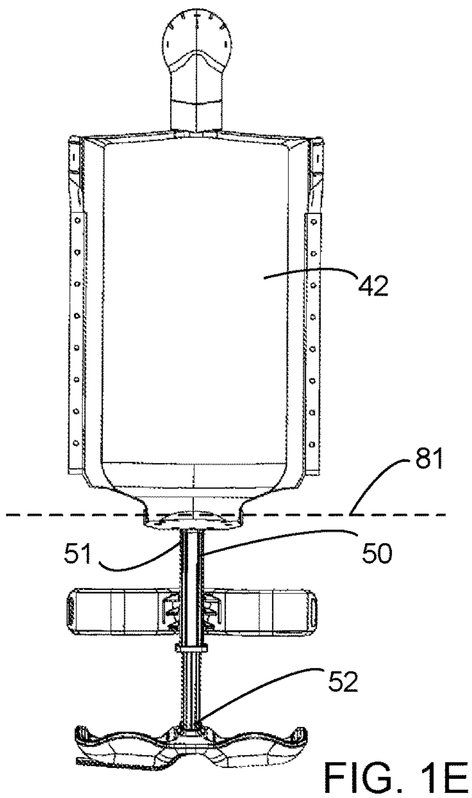
Figure 1F:
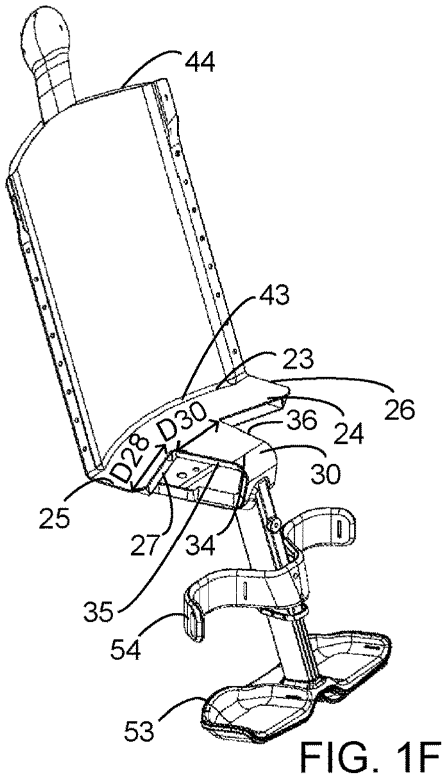
Figure 1G:
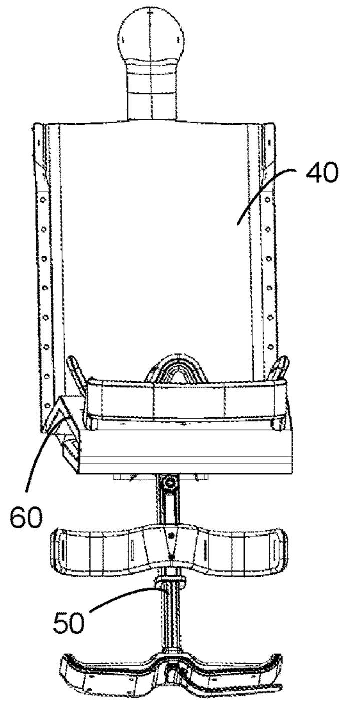
Figure 1H:
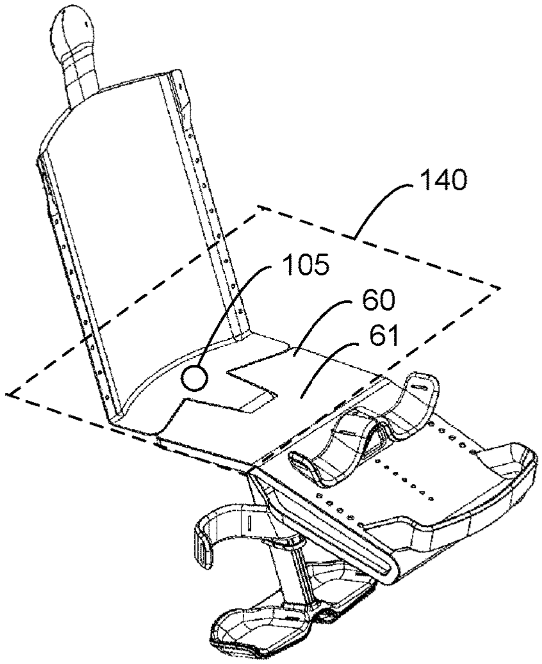
Figure 1I:
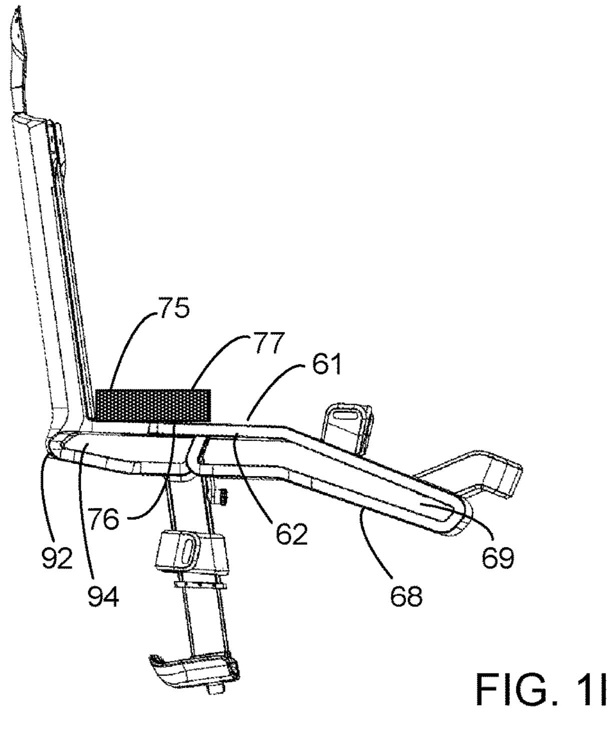
Figure 1J:
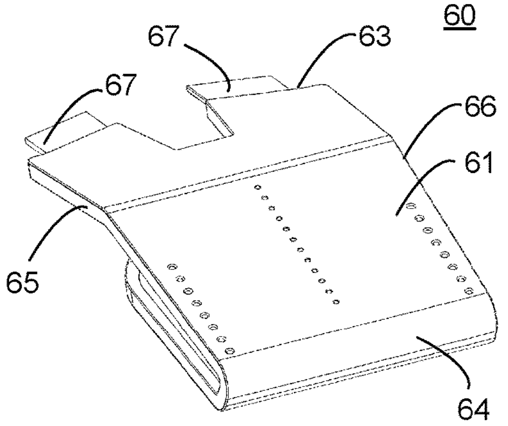

FIGS. 1A-1M illustrate various high level views of a teletherapy patient support 10, FIGS. 1A-1M being described together. Teletherapy patient support 10 comprises: a pelvis support member 20; an optional pelvis extension member 30; a torso support member 40; a first leg support 50; a second leg support 60; a control circuitry 70; an optional booster 75; a position rotation member 80; and an optional base support 90, exhibiting a first contact point 91, a second contact point 92 and a base member 93 extending between first contact point 91 and second contact point 92. FIG. 1A illustrates a high level perspective view of teletherapy patient support 10 with second leg support 60 detached. FIG. 1B illustrates a high level perspective view of teletherapy patient support 10 with second leg support 60 attached. FIGS. 1C-1F illustrate side, front, back and perspective views, respectively, of teletherapy patient support 10 with second leg support 60 detached. FIGS. 1G-1I illustrate front, perspective and side views, respectively, of teletherapy patient support 10 with second leg support 60 attached. FIG. 1J illustrates a perspective view of second leg support 60.

Pelvis support member 20 exhibits: a first face 21 and a second face 22, second face 22 opposing first face 21; a first side 23; a second side 24, second side 24 opposing first side 23; a third side 25; a fourth side 26, fourth side 26 opposing third side 25; and at least one receptacle 27. Each of first face 21 and second face 22 extends from first side 23 to second side 24 and from third side 25 to fourth side 26. In one embodiment, each receptacle 27 is a hole. In another embodiment (not shown), each receptacle 27 comprises a connection device arranged to receive a corresponding connection member. In one embodiment, a plurality of receptacles 27 is provided. In another embodiment, each receptacle 27 extends into second side 24 of pelvis support member 20 such that the respective receptacle 27 is sandwiched between first face 21 and second face 22. In one embodiment, pelvis support member 20 is constructed such that the distance between first side 23 and second side 24, denoted D20, is large enough to support the pelvis of a patient, yet small enough to allow the patient to be in a supine position when pelvis support member 20 and torso support member 40 are in a reclined position and to allow the patient to be in a standing position when pelvis support member 20 and torso support member 40 are in an upright position, as described below. In one further embodiment, distance D20 is less than 20 centimeters. In one yet further embodiment, distance D20 is between 10-20 centimeters.

Optional pelvis extension member 30 exhibits: a first face 31; a second face 32, second face 32 opposing first face 31; a first end 33; and a second end 34, second end 34 opposing first end 33; a first side 35; and a second side 36, second side 36 opposing first side 35. Each of first face 31 and second face 32 extends from first end 33 to second end 34 and from first side 35 to second side 36.

Torso support member 40 exhibits: a first face 41; a second face 42, second face 42 opposing first face 41; a first end 43; a second end 44, second end 44 opposing first end 43; a first side 45; and a second side 46, second side 46 opposing first side 45. Each of first face 41 and second face 42 extends from first end 43 to second end 44 and from first side 45 to second side 46. In one embodiment, torso support member further comprises an optional head support 47, exhibiting a first side 48 and a second side 49, second side 49 opposing first side 48. In one embodiment, the distance between first side 48 and second side 49 of head support 47 is smaller than the distance between first side 45 and second side 46 of torso support member 40. Head support 47 extends proximally from second end 44 away from first end 43.

First leg support 50 exhibits a first end 51 and a second end 52. In one embodiment, first leg support 50 comprises a foot support 53 at second end 52. In another embodiment first leg support 50 comprises a leg support 54 positioned between first end 51 and second end 52.

Second leg support 60 exhibits: a first face 61; a second face 62, second face 62 opposing first face 61; a first side 63; a second side 64, second side 64 opposes first side 63; a third side 65; a fourth side 66, fourth side 66 opposing third side 65; at least one connection member 67; and an optional base support 68. Each of first face 61 and second face 62 extends from first side 63 to second side 64 and from third side 65 to second side 66. In one embodiment, each connection member 67 extends proximally from first side 63 away from second side 64. Optional base support 68 is in contact with second face 62, preferably at opposing ends of optional base support 68, with a predetermined distance between optional base support 68 and second face 62 to add structural support to second leg support 60, which reduces the possibility of second leg support 60 being bent if excessive force is applied thereto. In one embodiment, second leg support 60 is constructed as a single piece. In another embodiment, an opening 69 is situated between second face 62 and optional base support 68.

In one embodiment (not shown), control circuitry 70 comprises a processor and a memory, the memory having stored thereon instructions that when read by the processor cause the processor to perform one or more actions. In another embodiment, control circuitry 70 comprises, without limitation, a micro-processor, a micro-controller, a field programmable gate array (FPGA) and/or an application specific integrated circuit (ASIC).

As illustrated in FIG. 1I, optional booster 75 exhibits a first face 76 and a second face 77, second face 77 opposing first face 76. In one embodiment (not shown), optional booster 75 comprises a plurality of boosters, stacked one on top of the other. In another embodiment, optional booster 75 comprises polyurethane.

In one embodiment (not shown), position rotation member 80 comprises a motor. In one further embodiment, the motor is in electrical communication with control circuitry 70, and responsive thereto. Position rotation member 80 is arranged to rotate about a position rotation axis 81. In another embodiment, position rotation member 80 is implemented as part of a robotic arm 82, exhibiting 6 degrees of freedom, with position rotation member 80 providing 1 or more of the 6 degrees of freedom. In one further embodiment, robotic arm 82 is implemented as described in PCT application publication S/N WO 2019/123464, published Jun. 27, 2019 and entitled "PATIENT POSITIONING APPARATUS AND METHOD", the entire contents of which are incorporated herein by reference. In one illustrated embodiment, position rotation member 80 comprises a pair of connection members 83, each connection member 83 connected to a respective side of a base 84. In such an embodiment, one or more motors are in mechanical communication with one, or both, connection members 83 and are arranged to rotate connection members 83 about position rotation axis 81, which extends through base 84. Position rotation member 80 is illustrated as being connected to optional base support 90, however this is not meant to be limiting in any way. In another embodiment, position rotation member 80 is connected to: pelvis support member 20; optional extension member 30; and/or torso support member 40.

In another embodiment (not shown) position rotation member 80 comprises a single rotational member connected to pelvis support member 20, the single rotational member arranged to rotate pelvis support member about position rotation axis 81. In one further embodiment, the single rotational member exhibits a spherical or elongated shape. In another embodiment (not shown), position rotation member 80 comprises a translatable mechanism arranged to be translated along a guide rail, the translatable mechanism connected to pelvis support member 20. In such an embodiment, the guide rail is shaped and configured such that movement of the translatable mechanism along the guide rail causes pelvis support member 20 to be rotated about position rotation axis 81. In one embodiment, position rotation axis 81 is substantially parallel to a floor 85. Teletherapy patient support 10 is positioned on floor 85.

Optional pelvis extension member 30 extends (e.g., proximally) from second side 24 of pelvis support member 20. In one embodiment, first end 33 of optional pelvis extension member 30 is connected to second side 24 of pelvis support member 20. In another embodiment, optional pelvis extension member 30 and pelvis support member 20 are constructed such that first end 33 of optional pelvis extension member 30 and second side 24 of pelvis support member 20 are the same. In one embodiment, each of first side 35 and second side 36 of optional pelvis extension member 30 exhibits an angle with second side 24 of pelvis support member 20 between 60-130 degrees. In one further embodiment, the angle with second side 24 is between 60-90 degrees. These acute angles allow for improved support of the thighs of a patient supported by pelvis support member 20. In one embodiment, first face 21 of pelvis support member 20 and first face 31 of optional pelvis extension member 30 form together a general T shape. Advantageously, the T shape allows a patient's legs to span sides 35 and 36 of optional pelvis extension member 30, which provides superior pelvic support. Additionally, the abdomen and pelvis of the patient are more exposed when in such a position, i.e. when the patient is standing, with their legs supported by first leg support 50. This allows improved access for a teletherapy irradiation beam to the abdomen/pelvis of the patient. In one embodiment, the distance between first side 35 and second side 36 of optional pelvis extension member decreases from first end 33 to second end 34. This allows more comfortable positioning of the patient's legs. In another embodiment, the distance between first side 35 and second side 36, at first end 33, is approximately ⅓ of the distance between third side 35 and second side 36, however this is not meant to be limiting in any way.

In another embodiment, optional pelvis extension member 30 separates second side 24 of pelvis support member 20 into a first section 28 and a second section 29. In one further embodiment, a pair of receptacles 27 is provided, a first receptacle 27 extending into first section 28 of second side 24 of pelvis support member 20 and a second receptacle 27 extending into second section 29 of second side 24. In another further embodiment, the distance between first section 28 and second section 29, i.e. the distance between first side 35 and second side 36, denoted D30, is less than a length of each of first section 28 and second section 29. Particularly, the distance between first side 35 of optional pelvis extension member 30 and third side 25 of pelvis support member 20, denoted D28, is less than D30. Similarly, the distance between second side 36 of optional pelvis extension member 30 and fourth side 26 of pelvis support member 20, denoted D29, is less than D30.

In one embodiment, as illustrated in FIG. 1H, pelvis support member 20 exhibits a hole 105 extending from first face 21 to second face 22. In another embodiment (not shown), optional pelvis extension member 30 exhibits hole 105 extending from first face 31 to second face 32. Hole 105 allows access to a patient supported by teletherapy patient support 10, including access for rectal devices.

Torso support member 40 extends from pelvis support member 20. In one embodiment, torso support member 40 extends from first side 23 of pelvis support member 20. In one further embodiment, first end 43 of torso support member 40 is connected to first side 23 of pelvis support member 20. In another further embodiment, torso support member 40 and pelvis support member 20 are constructed such that first end 43 of torso support member 40 and first side 23 of pelvis support member 20 are the same. In one embodiment, first face 41 is concavely curved, the concave curve extending from first side 45 to second side 46, such that a midline of first face 41 extending from first side 23 is further away from optional pelvis extension member 30 than a plane defined by first side 45 and second side 46. In one further embodiment, second face 42 is convexly curved, the convex curve extending from first side 45 to second side 46, such that a midline of second face 42 extending from first side 23 is further away from optional pelvis extension member 30 than the plane defined by first side 45 and second side 46. First face 41 of torso support member 40 faces first face 21 of pelvis support member 20, i.e. there is an angle of less than 180 degrees between first face 41 and first face 21. In one embodiment, the angle between first face 41 of torso support member 40 and first face 21 of pelvis support member 20 is greater than 90 degrees and less than 180 degrees. In one further embodiment, the angle between first face 41 of torso support member 40 and first face 21 of pelvis support member 20 is between 100-120 degrees. In one yet further embodiment, the angle between first face 41 of torso support member 40 and first face 21 of pelvis support member 20 is about 110 degrees.

First contact point 91 of optional base support 90 is in contact with pelvis support member 20, optionally at second side 24 thereof, and second contact point 92 of optional base support 90 is in contact with optional pelvis extension member 30, optionally at second end 34 thereof. In one embodiment, pelvis support member 20, optional pelvis extension member 30 and optional base support 90 are constructed as a single piece. In another embodiment, pelvis support member 20, optional pelvis extension member 30 and optional base support 90 are constructed such that: first contact point 91 of optional base support 90 and second side 24 of pelvis support member 20 are the same; and second contact point 92 of optional base support 90 and second end 34 of optional pelvis extension member 30 are the same. In one embodiment, pelvis support member 20, optional pelvis extension member 30 and optional base support 90 are constructed such that an opening 94 is created between base member 93 and a surface defined by second face 22 of pelvis support member 20 and second face 32 of optional pelvis extension member 30.

First leg support 50 extends from pelvis support member 20 at first end 51 thereof. In one embodiment, first leg support 50 extends from base member 93 of optional base support 90. First leg support 50 faces second face 24 of pelvis support member 20, i.e. there is an angle less than 180 degrees between first leg support 50 and second face 22.

The at least one connection member 67 of second leg support 60 is arranged to be alternately: positioned within the at least one receptacle 27 of pelvis support member 20; and not positioned within the at least one receptacle 27 of pelvis support member 20. Specifically, each connection member 67 is shaped and sized so as to fit within a respective receptacle 27, and be removable therefrom. In one embodiment, connection members 67 and respective receptacles 27 are shaped and sized such that second leg support 60 is secured to pelvis support member 20. In another embodiment (not shown), additional fastening elements are provided. In one further embodiment, these fastening elements include: spring controlled elements within receptacles 27; and/or bolts or other locking mechanisms external to pelvis support member 20 and second leg support 60.

Figure 1K:
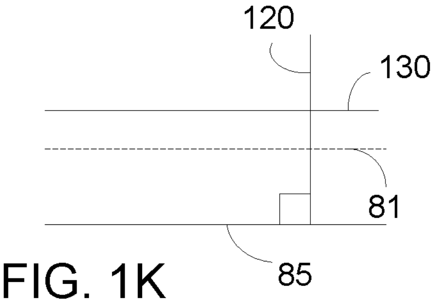
Figure 1L:
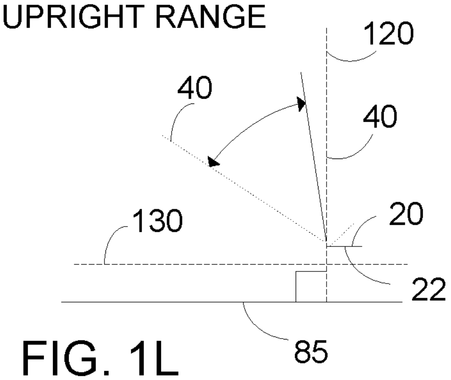
Figure 1M:
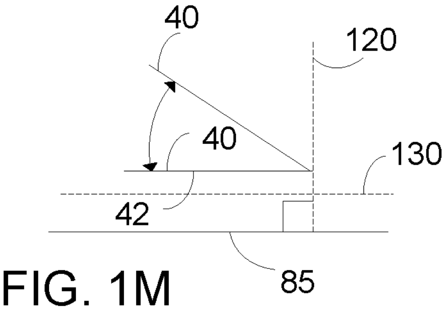

In operation, control circuitry 70 controls position rotation member 80 to rotate pelvis support member 20 and torso support member 40 about position rotation axis 81 by: an upright angle range as illustrated in FIG. 1L; and a reclined angle range, as illustrated in FIG. 1M, the upright angle range different than the reclined angle range. The upright angle range and the reclined angle range are respective defined in relation to a vertical plane 120 extending vertically from floor 85, and a horizontal plane 130 extending parallel to floor 85, as shown in FIG. 1K. Vertical plane 120 is generally perpendicular to position rotation axis 81 and horizontal plane 130 is generally parallel to position rotation axis 81. The upright angle range as shown in FIG. 1L contains the angles of torso support member 40 in relation to vertical plane 120. The angles of torso support member 40 in relation to vertical plane 120 in the upright angle range are smaller than the angles of torso support member 40 in relation to vertical plane 120 in the reclined angle range. Similarly, the reclined angle range, as shown in FIG. 1M, contains the angles of torso support member 40 in relation to horizontal plane 130. The angles of torso support member 40 in relation to horizontal plane 130 in the reclined angle range are smaller than the angles of torso support member 40 in relation to horizontal plane 130 in the upright angle range.

In one embodiment, a first end of the upright angle range coincides with second face 22 of pelvis support member 20 generally facing floor 85. Thus, first face 41 of torso support member 40 exhibits an angle of 10-30 degrees with vertical plane 120, depending on the angle between torso support member 40 and pelvis support member 20. For example, if first face 41 of torso support member 40 exhibits an angle of 20 degrees with first face 21 of pelvis support member 20, the first end of the upright angle range coincides with first face 41 exhibiting a 110 degree angle with vertical plane 120. In one further embodiment, a first end of the reclined angle range coincides with torso support member 40 being parallel with horizontal plane 130. In another further embodiment, a second end of the upright angle range and a second end of the reclined angle range are both approximately 40 degrees from vertical plane 120 and 50 degrees from horizontal plane 130, with second face 42 of torso support member 40 facing floor 85. In another embodiment, the upright angle range and the reclined angle range partially overlap.

In one embodiment, robotic arm 82 is arranged, responsive to control circuitry 70, to rotate pelvis support member 20 about an axis 125 by a predetermined range, optionally 10 degrees to either side of axis 125. Axis 125 is perpendicular to vertical plane 120 and parallel to horizontal plane 130. In another embodiment, robotic arm 82 is arranged, responsive to control circuitry 70 to rotate pelvis support member 20 about an axis 135 by a predetermined range, optionally 360 degrees. Axis 135 is parallel to vertical plane 120 and perpendicular to horizontal plane 130.

Second leg support 60 is detachable from pelvis support member 20 by removing connection members 67 from the respective receptacles 27. When desired, second leg support 60 is again attached by positioning connection members 67 within the respective receptacle 27. In one embodiment, first face 21 of pelvis support member 20 defines a plane 140 and the attached second leg support 60 extends along plane 140 when connection members 67 are positioned within the respective receptacles 27 of pelvis support member 20. Having second leg support 60 extend along plane 140, defined by pelvis support member 20, allows the patient to sit in a more comfortable position when a portion of the torso is being irradiated. When pelvis support member 20 is rotated about position rotation axis 81 to be within the reclined angle range, i.e. a patient supported by teletherapy patient support 10 is lying down, second leg support 60 is detached from pelvis support member 20 and the patient's legs are supported by first leg support 50. When pelvis support member 20 is rotated about position rotation axis 81 to be within the upright angle range, the patient supported by teletherapy patient support 10 can either be in a sitting position or a standing position. In the event that the patient is in a standing position, second leg support 60 is detached from pelvis support member 20 and the patient's legs are supported by first leg support 50. In the event that the patient is in a sitting position, second leg support 60 is attached to pelvis support member 20 and the patient's legs are supported by second leg support 60.

In one embodiment, when a patient is in a sitting position, first face 76 of optional booster 75 is in contact with first face 21 of pelvis support member 20 and the patient sits on second face 77 of optional booster 75. The height of optional booster 75, i.e. the distance between first face 76 and second face 77, is sized such that the head of the patient rests against head support 47. Advantageously, by providing optional booster 75, a non-adjustable head support 47 can be used. This provides a stronger structure for torso support member 40 and head support 47.

In another embodiment, in order to position the patient in a sitting position, control circuitry 70 controls position rotation member 80 to rotate pelvis support member 20 about position rotation axis 81 by a predetermined angle within the reclined angle range, e.g. 90 degrees away from vertical axis 120. Subsequent to rotating pelvis support member 20 by the predetermined angle within the reclined angle range, the patient is positioned on first face 21 of pelvis support member 20. Optionally, prior to positioning the patient, optional booster 75 is positioned on first face 21 of pelvis support member 20 and the patient is positioned on optional booster 75. Subsequent to positioning the patient on pelvis support member 20, control circuitry 70 controls position rotation member 80 to rotate pelvis support member 20 about position rotation axis 81 to a predetermined angle within the upright angle range. For example, pelvis support member 20 is first rotated 90 degrees from vertical axis 120. The patient is then loaded onto pelvis support member 20 in a supine position and pelvis support member 20 is rotated 70 degrees towards vertical axis 120. Pelvis support member 20 is thus positioned such that torso support member 40 exhibits an angle of about 20 degrees with vertical axis 120 and the patient is in a semi-standing position and supported by first leg support 50. The patient's legs are then raised and second leg support 60 is attached to pelvis support member 20 to thereby transition the patient to a sitting position.

Teletherapy patient support 10 is thus arranged to support a patient for teletherapy in multiple positions, including reclined, sitting and standing. Advantageously, the patient can be irradiated by a treatment beam and imaged by a 3D imager, including a computed tomography (CT) imager. For example, in order to irradiate a growth in the pelvis of patient, the patient can be imaged by a CT imager in a standing position, which allows full access to the pelvis. The irradiation can then be performed in a sitting position, which is more comfortable for the patient.

The above has been described in an embodiment where teletherapy patient support 10 is switched between 3 positions: standing; sitting; and supine. However, this is not meant to be limiting in any way. In another embodiment, pelvis support member 20 isn't rotated into a supine position. In such an embodiment, teletherapy patient support 10 exhibits 2 positions: a standing position, where second leg support 60 is detached from pelvis support member 20; and a sitting position, where second leg support 60 is attached to pelvis support member 20.

Figure 2A:
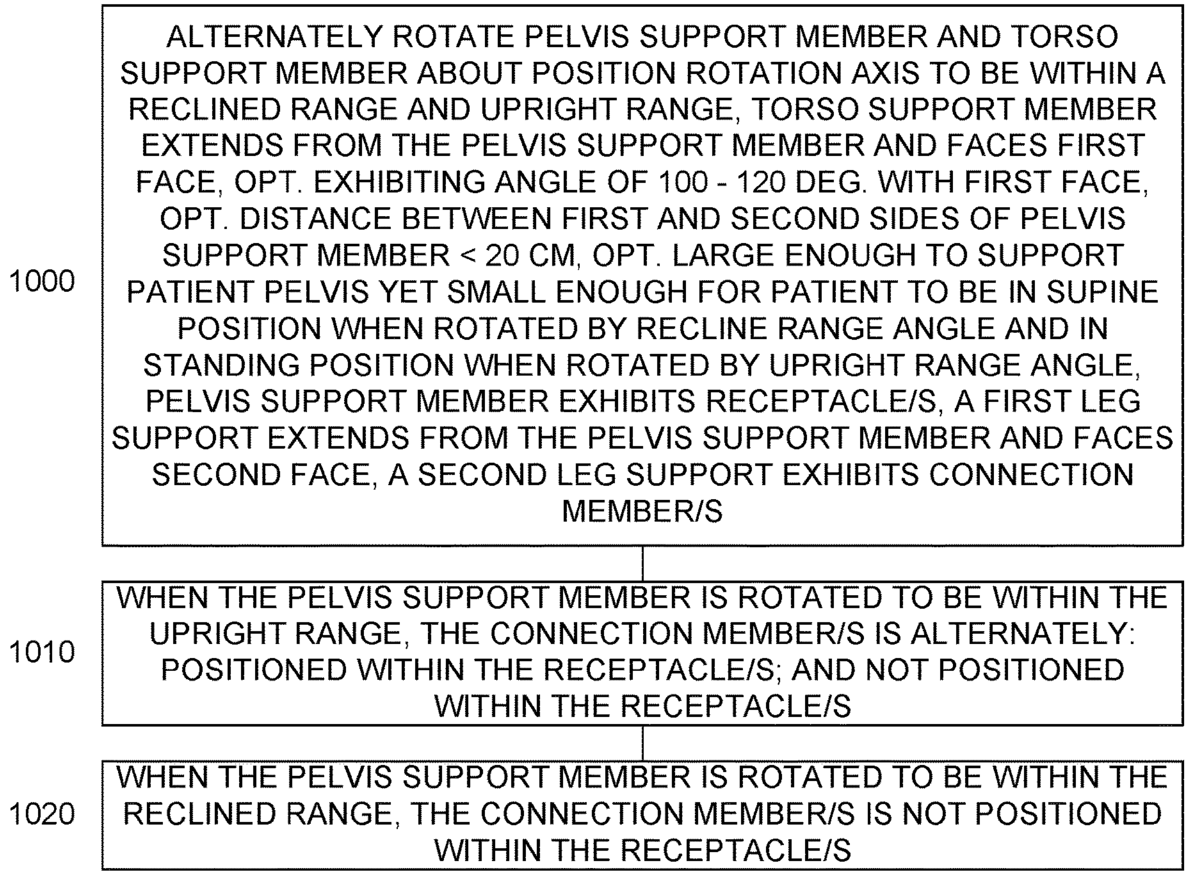
FIG. 2A illustrates a high level flow chart of a first teletherapy patient support method, in accordance with certain embodiments.

FIG. 2A illustrates a high-level flow chart of a first teletherapy patient support method, in accordance with certain embodiments. The method of FIG. 2A may be conducted using teletherapy patient support 10, disclosed herein above. In stage 1000, a pelvis support member and a torso support member are alternately rotated about a position rotation axis to be within an upright angle range and a reclined angle range, the reclined angle range is different than the upright angle range. As described above, in one embodiment the upright angle range and the reclined angle range partially overlap. The pelvis support member exhibits a first face and a second face, the second face opposing the first face. A torso support member extends from the pelvis support member and faces the first face of the pelvis support member. Optionally, the torso support member exhibits a first end and a second end, the second end opposing the first end.

The pelvis support member further exhibits a first side and a second side, the second side opposing the first side. In one embodiment, the distance between the first side and the second side of the pelvis support member is less than 20 centimeters. In another embodiment, the distance between the first side and the second side of the pelvis support member is large enough to support the pelvis of a patient, yet small enough to: allow the patient to be in a supine position when the pelvis support member and the torso support member are rotated about the position rotation axis by an angle within the reclined angle range; and allow the patient to be in a standing position when the pelvis support member and the torso support member are rotated about the position rotation axis by an angle within the upright angle range. Additionally, the pelvis support member further exhibits at least one receptacle.

A first leg support extends from the pelvis support member and faces the second face of the pelvis support member. A second leg support exhibits at least one connection member. In one embodiment, a pelvis extension member extends from the second side of the pelvis support member. In one further embodiment, the torso support member exhibits an angle with the pelvis extension member between 100-120 degrees.

In stage 1010, when the pelvis support member and torso support member of stage 1000 are rotated about the position rotation axis to be within the upright angle range, the at least one connection member of the second leg support is alternately: positioned within the at least one receptacle of the pelvis support member; and not positioned within the at least one receptacle of the pelvis support member. In stage 1020, when the pelvis support member and torso support member of stage 1000 is rotated about the position rotation axis to be within the reclined angle range, the at least one connection member of the second leg support is not positioned within the at least one receptacle of the pelvis support member.

Figure 2B:
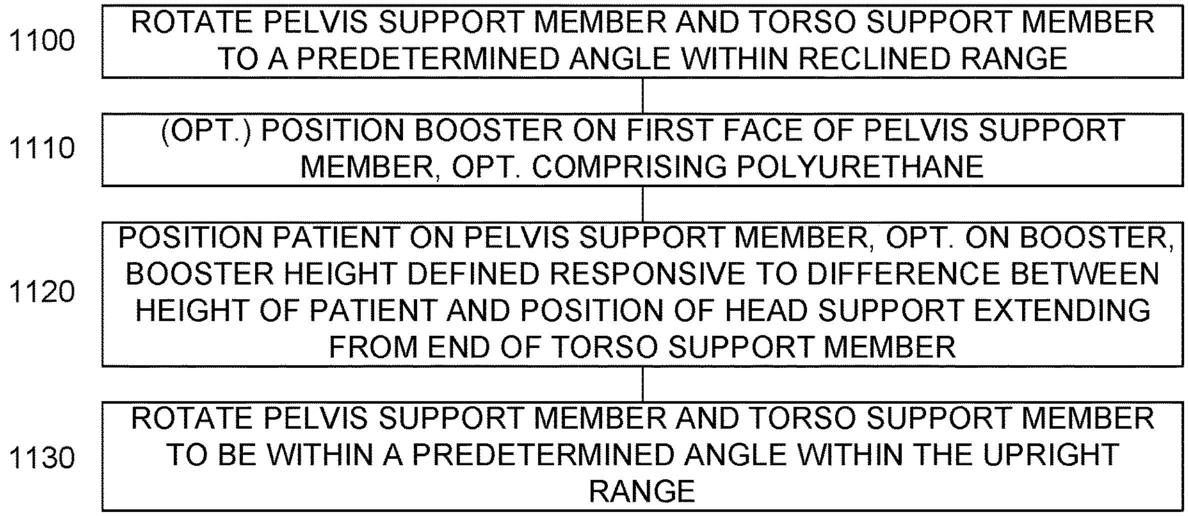
FIG. 2B illustrates a high level flow chart of a method of loading a patient into a sitting position, in accordance with certain embodiments.

FIG. 2B illustrates a high-level flow chart of a method of positioning a patient on the patient support member (e.g., patient support member 10 disclosed herein above) of stage 1000. In stage 1100, the pelvis support member and torso support member of stage 1000 are rotated about the position rotation axis to a predetermined angle within the reclined angle range of stage 1000. In optional stage 1110, a booster is positioned on the first face of the pelvis support member. Optionally, the positioned booster comprises polyurethane. In stage 1120, subsequent to the rotation of stage 1100, the patient is positioned on the pelvis support member, optionally on the positioned booster of optional stage 1100. In such an embodiment, the height of the positioned booster is defined responsive to a difference between a height of the patient and a position of a head support, the head support extending from the second end of the torso support member of stage 1000. In stage 1130, subsequent to the positioning of the patient of stage 1120, the pelvis support member and torso support member are rotated about the position rotation axis to a predetermined angle within the upright angle range.

FIG. 2C illustrates a high level flow chart of a second teletherapy patient support method, in accordance with certain embodiments. The method of FIG. 2C may be conducted using teletherapy patient support 10, discussed herein above. In stage 2000, at least one connection member of a second leg support is alternately: positioned within at least one receptacle of the pelvis support member; and not positioned within the at least one receptacle of the pelvis support member. As described above in relation to stage 1000, the pelvis support member exhibits a first face and a second face, the second face opposing the first face. As further described above, a torso support member extends from the pelvis support member and faces the first face of the pelvis support member. The pelvis support member further exhibits a first side and a second side, the second side opposing the first side. As further described above, a first leg support extends from the pelvis support member and faces the second face of the pelvis support member.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A teletherapy patient support comprising:
- a pelvis support member exhibiting a first face and a second face opposing said first face;
- a torso support member extending from said pelvis support member and facing said first face of said pelvis support member;
- a first leg support extending from said pelvis support member and facing said second face of said pelvis support member; and
- a second leg support exhibiting at least one connection member,
- wherein said pelvis support member exhibits at least one receptacle, said second leg support arranged to be alternately:
  - attached to said pelvis support member by said at least one connection member being positioned within said at least one receptacle of said pelvis support member; and
  - detached from said pelvis support member by said at least one connection member not being positioned within said at least one receptacle of said pelvis support member.

2. The teletherapy patient support of claim 1, further comprising a pelvis extension member,
- wherein said pelvis support member further exhibits a first side and a second side opposing said first side, each of said first face and said second face extending from said first side to said second side, and
- wherein said torso support member extends from said first side of said pelvis support member and said pelvis extension member extends from said second side of said pelvis support member.

3. The teletherapy patient support of claim 2, wherein said at least one receptacle of said pelvis support member extends into said second side thereof.

4. The teletherapy patient support of claim 3, wherein said second side of said pelvis support member exhibits a first section and a second section, said pelvis extension member separating said second section from said first section, and
- wherein said at least one receptacle of said pelvis support member exhibits a pair of receptacles, each of said pair of receptacles extending into a respective one of said first section and said second section of said second side of said pelvis support member.

5. The teletherapy patient support of claim 2, wherein a distance between said first side and said second side of said pelvis support member is less than 20 centimeters.

6. The teletherapy patient support of claim 2, further comprising:
- a control circuitry; and
- a position rotation member, said control circuitry arranged to control said position rotation member to alternately rotate said pelvis support member and said torso support member about a position rotation axis by:
  - an upright angle range, and
  - a reclined angle range different than said upright angle range,
- wherein a distance between said first side and said second side of said pelvis support member is large enough to support the pelvis of a patient, yet small enough to:
  - allow the patient to be in a supine position when said pelvis support member and said torso support member are rotated about said position rotation axis by an angle within said reclined angle range; and
  - allow the patient to be in a standing position when said pelvis support member and said torso support member are rotated about said position rotation axis by an angle within said upright angle range.

7. The teletherapy patient support of claim 2, wherein said torso support member exhibits an angle with said pelvis extension member between 100 to 120 degrees.

8. The teletherapy patient support of claim 2, wherein said first face of said pelvis support member and a face of said pelvis extension member form a general T shape.

9. The teletherapy patient support of claim 2, wherein said second side of said pelvis support member exhibits a first section and a second section, said pelvis extension member separating said second section from said first section.

10. The teletherapy patient support of claim 2, wherein said pelvis extension member exhibits a first face and a second face opposing said first face, and
- wherein said pelvis support member or said pelvis extension member exhibits a hole extending from said respective first face to said respective second face.

11. The teletherapy patient support of claim 1, further comprising:
- a control circuitry; and
- a position rotation member, said control circuitry arranged to control said position rotation member to alternately rotate said pelvis support member and said torso support member about a position rotation axis by:
  - an upright angle range, and
  - a reclined angle range different than said upright angle range.

12. The teletherapy patient support of claim 1, wherein said first face of said pelvis support member generally defines a plane and said second leg support extends along said plane when said at least one connection member of said second leg support is positioned within said at least one receptacle of said pelvis support member.

13. A teletherapy patient support method, wherein a pelvis support member exhibits a first face and a second face opposing the first face,
- wherein a torso support member extends from the pelvis support member and faces the first face of the pelvis support member,
- wherein a first leg support extends from the pelvis support member and faces the second face of the pelvis support member,
- wherein said pelvis support member further exhibits at least one receptacle, wherein a second leg support exhibits at least one connection member, and wherein the method comprises, alternately:

positioning the at least one connection member of the second leg support within the at least one receptacle of the pelvis support member; and not positioning the at least one connection member of the second leg support within the at least one receptacle of the pelvis support member.

14. The method of claim 13, further comprising alternately rotating a pelvis support member about a position rotation axis by:

an upright angle range; and a reclined angle range different than said upright angle range, wherein said alternately positioning and not positioning the at least one connection member of the second leg support within the at least one receptacle of the pelvis support member is performed when the pelvis support member is rotated about the position rotation axis by an angle within said upright angle range, and wherein, when the pelvis support member is rotated about said position rotation axis by an angle within said reclined angle range, the method further comprises not positioning the at least one connection member of said second leg support within the at least one receptacle of said pelvis support member.

15. The method of claim 14, further comprising alternately rotating a pelvis support member about a position rotation axis by:

an upright angle range; and a reclined angle range different than said upright angle range, wherein a distance between the first side and the second side of the pelvis support member is large enough to support the pelvis of a patient, yet small enough to:

allow the patient to be in a supine position when the pelvis support member and the torso support member are rotated about the position rotation axis by an angle within the reclined angle range; and allow the patient to be in a standing position when the pelvis support member and the torso support member are rotated about the position rotation axis by an angle within the upright angle range.

16. The method of claim 14, further comprising alternately rotating a pelvis support member about a position rotation axis by:

an upright angle range; and a reclined angle range different than said upright angle range, wherein the method further comprises:

rotating the pelvis support member about the position rotation axis by a predetermined angle within said reclined angle range;

subsequent to said rotation by said predetermined angle within said reclined angle range, positioning a patient on said positioned booster; and subsequent to said positioning of said patient, rotating the pelvis support member about the position rotation axis to a predetermined angle within said upright angle range.

* * * * *